US012569159B2

(12) United States Patent
Mena Benito et al.

(10) Patent No.: US 12,569,159 B2
(45) Date of Patent: Mar. 10, 2026

(54) MAGNETIC RESONANCE GUIDED SELECTION OF VIRTUAL REALITY MOTION PATTERNS FOR PHANTOM LIMBS

(71) Applicant: KONINKLIJKE PHILIPS N.V., Eindhoven (NL)

(72) Inventors: Maria Estrella Mena Benito, Eindhoven (NL); Raymond van Ee, Geldrop (NL); Adrianus Johannes Maria Dennissen, Moergestel (NL); Timmy Robertus Maria Leufkens, Upplands Vasby (SE); Evelijne Machteld Hart de Ruijter-Bekker, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/728,135

(22) PCT Filed: Dec. 27, 2022

(86) PCT No.: PCT/EP2022/087853
§ 371 (c)(1),
(2) Date: Jul. 11, 2024

(87) PCT Pub. No.: WO2023/135011
PCT Pub. Date: Jul. 20, 2023

(65) Prior Publication Data
US 2025/0090040 A1      Mar. 20, 2025

(30) Foreign Application Priority Data
Jan. 14, 2022    (EP) ..................................... 22151487

(51) Int. Cl.
| | |
|---|---|
| A61B 5/055 | (2006.01) |
| A61B 5/00 | (2006.01) |
| G01R 33/48 | (2006.01) |

(52) U.S. Cl.
CPC ............ *A61B 5/055* (2013.01); *A61B 5/0042* (2013.01); *G01R 33/4818* (2013.01)

(58) Field of Classification Search
CPC .... A61B 5/055; A61B 5/0042; G01R 33/4818
See application file for complete search history.

(56) References Cited

U.S. PATENT DOCUMENTS

| | | |
|---|---|---|
| 6,018,675 A | 1/2000 | Apkarian et al. |
| 7,302,296 B1 | 11/2007 | Hoffer |

(Continued)

FOREIGN PATENT DOCUMENTS

| | | |
|---|---|---|
| FR | 2892940 A1 | 5/2007 |

OTHER PUBLICATIONS

International Search Report and Written Opinion from PCT/EP2022/087853 mailed May 9, 2023.

(Continued)

*Primary Examiner* — Sean A Frith

(57) ABSTRACT

Disclosed herein is a medical instrument (100) comprising a magnetic resonance imaging system (102) configured for acquiring k-space data (148, 152, 166) of a brain of a subject (118) with a missing limb (128) and a complementary limb (129) and a virtual reality system (122). The execution of machine executable instructions causes a computational system (132) to: identify (210) a complementary limb functional region (156) using functional magnetic resonance imaging and determine (212) a phantom limb functional region (158) in the brain by applying brain symmetry. Execution of the machine executable instructions causes the computational system to perform repetitions of: reconstruct- (Continued)

ing (218) a phantom limb functional magnetic resonance image (168) from the phantom limb k-space data (166) acquired during the display of repetition specific motion patterns of the missing limb using the virtual reality system; and assigning (220) a numerical score (170) to the repetition specific movement pattern by detecting neural activity in the phantom limb functional region. Execution of the machine executable instructions further causes the computational system to construct (224) at least one virtual reality motion sequence (180) of the missing limb by selecting the varied movement parameters using the numerical score.

17 Claims, 4 Drawing Sheets

(56) References Cited

U.S. PATENT DOCUMENTS

| | | | |
|---|---|---|---|
| 2011/0065505 A1 | 3/2011 | Solanki et al. | |
| 2011/0152249 A1* | 6/2011 | Borsook | A61B 5/4821 |
| | | | 514/217 |
| 2015/0201879 A1* | 7/2015 | Hargrove | A61B 5/7257 |
| | | | 600/411 |
| 2016/0121160 A1 | 5/2016 | Hyslop et al. | |
| 2016/0302720 A1 | 10/2016 | John et al. | |
| 2017/0365101 A1* | 12/2017 | Samec | G16H 20/70 |
| 2018/0182094 A1 | 6/2018 | Parra et al. | |
| 2018/0301057 A1 | 10/2018 | Hargrove et al. | |
| 2020/0016363 A1* | 1/2020 | Macri | A61M 21/00 |
| 2020/0360655 A1 | 11/2020 | Shuster et al. | |

OTHER PUBLICATIONS

Christelle Cre'ac'h, Patrick Henry, Jean Marie Caille', and Miche'le Allard "Functional MR Imaging Analysis of Pain-related Brain Activation after Acute Mechanical Stimulation" AJNR Am J Neuroradiol 21:1402-1406, Sep. 2000.

Andoh Jamila et al: "Assessment of cortical reorganization and preserved function in phantom limb pain: a methodological perspective" Scientific Reports, vol. 10, No. 1, Dec. 1, 2020 (2020-12-01), pp. 1-15.

Adaikkammai set al: "Virtual Reality in Rehabilitating Amputees Suffering from Phantom Limb Pain", 2019 11th International Conference on Communication Systems & Networks (COMSNETS), IEEE, Jan. 7, 2019 (Jan. 7, 2019), pp. 801-806.

Andoh et al."Assessment of cortical reorganization and preserved function in phantom limb pain: a methodological perspective", arxiv.org, Cornell University Library, 201 Olin Library Cornell University Ithaca, NY 14853, Feb. 19, 2019 (Feb. 19, 2019).

Ramachandran et al "Reflections on Hand Pain" Elsevier Science Publishers, Amsterdam, Nl, vol. 149, No. 2, May 1, 2010 (May 1, 2010), pp. 171-172.

Siddel L. The challenge and management of phantom limb pain after amputation. British Journal of Nursing , 2012, 13(11) 664.

Ziegler-Graham K, Mackenzie EJ, Ephraim PL, et al. Estimating the prevalence of limb loss in the United States: 2005 to 2050. Arch Phys Med Rehabil. 2008;89:422-429.

Nikolajsen L, Jensen TS. Phantom limb pain. Br J Anaesth. 2001;87:107-116.

Flor H et al. Phantom limb pain: a case of maladaptive CNS plasticity? Nat.Rev.Neurosci. 2006, 7(11), 873.

Russell et al., Current theories and treatments for PLP, The Journal of Clinical Investigation, 2018, 128; 2168.

Ambron et al., 2018. Immersive Low-Cost Virtual Reality Treatment for Phantom Limb Pain: Evidence from Two Cases Frontiers in Neurology, doi: 10.3389/fneur.2018.00067.

* cited by examiner

MAGNETIC RESONANCE GUIDED SELECTION OF VIRTUAL REALITY MOTION PATTERNS FOR PHANTOM LIMBS

CROSS REFERENCE TO RELATED APPLICATIONS

This application is a U.S. national phase application of International Application No. PCT/EP2022/087853 filed Dec. 27, 2022, which claims the benefit of EP Application Serial No. 22151487.0 filed on Jan. 14, 2022 and is incorporated herein by reference.

FIELD OF THE INVENTION

The invention relates to functional magnetic resonance imaging, in particular to the use of magnetic resonance imaging for selecting movement patterns for maximizing neural activity in a phantom limb function region of a brain.

BACKGROUND OF THE INVENTION

Magnetic Resonance Imaging (MRI) may be used to measure detailed visualizations of the anatomical structure of a subject as well as directly measuring some biochemical reactions within the subject. For example, MRI can be used to measure the Hemodynamic response function within the brain to map neural activity. MRI techniques that measure neural activity within the brain are referred to herein as functional magnetic resonance imaging protocols for measuring brain activity.

United States patent application publication U.S. Pat. No. 20110065505 A1 discloses a visual feedback systems and methods implementing the system are disclosed that use computer generated images of lost limbs to display visual images of the limb being used in activities on a display unit providing visual feedback of the use of the missing limb to the brain to ameliorate, reduce, treat or eliminate phantom limb pain.

SUMMARY OF THE INVENTION

The invention provides for a medical instrument, a method, and a computer program product in the independent claims. Embodiments are given in the dependent claims.

One drawback to using virtual reality in treating phantom limb pain as described in, U.S. Pat. No. 20110065505 A1, is that the individual patient's characteristics are not used in designing movements in the virtual reality environment. Examples may provide for means of empirically determining movements in virtual reality that optimize the subject's neural response.

In one aspect the invention provides for a medical instrument that comprises a magnetic resonance imaging system that is configured for acquiring k-space data of a brain of a subject with a missing limb and a complimentary limb. The acquiring of the k-space data of a brain may be equivalent to saying that the imaging system is configured to acquire the k-space data from a field of view that encompasses the brain of the subject. A missing limb, as used herein, encompasses a limb that was previously part of the subject but then was disconnected or amputated from the subject. A complimentary limb, as used herein, is a limb of the subject that is complete and is the mirror image or symmetrical limb of the missing limb. For example, if the subject were missing a left hand, the left hand would be the missing limb and the complimentary limb would be the right hand. If the subject were missing the lower portion of the right leg, then the missing limb would be the lower portion of the right leg and the complimentary limb would be the lower portion of the left leg.

The medical instrument further comprises a virtual reality system that is configured for presenting a virtual reality image to the subject during acquisition of the k-space data. That is to say the virtual reality system is magnetic resonance imaging compatible and the subject to wear the virtual reality system such that the virtual reality is presented to the subject during the acquisition of the k-space data. This for example may be used by having screens and a data transfer to the virtual reality system such that they do not interfere with the magnetic resonance imaging. Virtual reality systems which are compatible with magnetic resonance imaging systems have been previously developed.

The medical instrument further comprises a memory for storing machine-executable instructions and pulse sequence commands. The pulse sequence commands are configured to acquire the k-space data according to a functional magnetic resonance imaging protocol for measuring brain activity.

The medical instrument further comprises a computational system that is configured for controlling the medical instrument. Execution of the machine-executable instructions causes the computational system to acquire baseline k-space data by controlling the magnetic resonance imaging system with the pulse sequence commands. The baseline k-space data is acquired to acquire baseline measurements of brain activity when the subject is inactive. For example, the operator or the system could instruct the subject to lay still and also the virtual reality system could for example be controlled such that the subject does not see any images of limbs or body parts or may for example display a pleasing or pleasant image or may present a dark image to the subject. For example, the virtual reality system during this step could be controlled to display a neutral or blank image.

Execution of the machine-executable instructions further causes the computational system to reconstruct a baseline functional magnetic resonance image from the baseline k-space data. The means of reconstructing the baseline functional magnetic resonance image would vary from protocol-to-protocol that is used for acquiring the k-space data. Execution of the machine-executable instructions further causes the computational system to acquire reference k-space data by controlling the magnetic resonance imaging system with the pulse sequence commands. During the acquisition of the reference k-space data with respect to the complimentary limb is acquired. Execution of the machine-executable instructions further causes the computational system to control the virtual reality system to generate images of the complimentary limb moving during acquisition of the reference k-space data.

It should be noted that a favorable example would be an instrument that is configured such that as the subject moves his or her complimentary limb and the system tracks the position of this complimentary limb. The virtual reality system would then render the position of the complimentary limb in the virtual world or images that are rendered to the subject. This may, in many instances, be impractical in a magnetic resonance imaging because the space within the magnetic resonance imaging system and the bore, particularly if it's a cylindrical magnet, may be limited. However, the mere displaying of the image of the complimentary limb moving will be enough to activate this portion of the subject's brain (the complimentary limb functional region) that is responsible for the movement and sensing the movement.

Execution of the machine-executable instructions further causes the computational system to reconstruct a reference functional magnetic resonance image from the reference k-space data. The reference functional magnetic resonance image is then a functional magnetic resonance image which maps what portions of the subject's brain are active when the complimentary limb is moved. As was noted before, the optimal situation would be for the subject to move his or her complimentary limb during the acquisition of the reference k-space data. However, this is not necessary. Execution of the machine-executable instructions further causes the computational system to identify a complementary limb functional region in the brain by comparing the baseline functional magnetic resonance image and the reference functional magnetic resonance image. By seeing how the baseline functional magnetic resonance image differs from the reference functional magnetic resonance image the complementary limb functional region of the brain is identified.

The complementary limb functional region in the brain is the region of the brain responsible for moving and sensing movement of the complimentary limb. Execution of the machine-executable instructions further causes the computational system to determine a phantom limb functional region of the brain by applying brain symmetry to the complementary limb functional region. In this step, a brain symmetry is determined from the brain and a mirroring process or mirror image transformation is used to transfer the complementary limb functional region to determine the phantom limb functional region.

It is also noted that in these steps the acquisition of the k-space data is described in terms of determining functional magnetic resonance imaging data. It is understood that during this process one or more anatomical magnetic resonance images of the subject's brain may also be acquired. For example, a magnetic resonance image which shows proton density as well as T1 or T2-weighting may be used to map the physical structure of the subject's brain. This for example may be performed by acquiring additional k-space data using additional pulse sequence commands that are configured for acquiring such an image. This may be used for developing an anatomical structure of the brain, which is then used for the mirror imaging process. The acquisition of k-space data during functional imaging may also involve acquiring k-space such that various images and curves (such as the Hemodynamic response function) can be measured. The exact measurements are dependent upon the type of functional magnetic resonance imaging protocol chosen.

Execution of the machine-executable instructions further causes the computational system to perform repetitions of acquiring phantom limb k-space data descriptive of the phantom limb functional region by controlling the magnetic resonance imaging system with the pulse sequence commands. For example, once the phantom limb functional region is known the field of view for the pulse sequence commands could be adjusted to acquire k-space data for the phantom limb functional region. This may be useful for example in accelerating the acquisition of the phantom limb k-space data. This however is optional and not necessary. Execution of the machine-executable instructions further causes the computational system to control the magnetic resonance imaging system to control the virtual reality system to generate images of the missing limb moving during acquisition of the phantom limb k-space data using a repetition-specific movement pattern of the missing limb with varied movement patterns for each repetition. In other words, during each repetition of the steps which are described, a different movement pattern of the missing limb is presented to the subject using the virtual reality system.

Next, execution of the machine-executable instructions further causes the computational system to reconstruct a phantom limb functional magnetic resonance image from the phantom limb k-space data. This is a repetition-specific phantom limb functional magnetic resonance image. During each loop a different image for the phantom limb functional magnetic resonance image is reconstructed. Execution of the machine-executable instructions further causes the computational system to assign a numerical score to the repetition-specific movement patterns for the current repetition by detecting neural activity in the phantom limb functional region of the phantom limb functional magnetic resonance image, the score being representative of the phantom limb functional image region. This could for example be done by comparing the amount of neural activity within this region in comparison to the baseline functional magnetic resonance image or a later acquired baseline functional magnetic resonance image.

After various loops of these are performed, the neural activity for different combinations of movements of the subject's phantom limb, as presented by the virtual reality system, are measured and provided a numerical score. This enables a detailed analysis of which movements elicit the largest response in the subject's brain within the phantom limb functional magnetic resonance image. This therefore enables the selection of virtual movements of this missing limb which most stimulate the subject's brain. Execution of the machine-executable instructions further causes the computational system to construct at least one virtual reality motion sequence of the missing limb by selecting the very movement patterns that maximize neural activity in the phantom limb functional region using the numerical score for each repetition-specific movement pattern.

This may be beneficial because the movements which maximize the neural activity in the phantom limb functional magnetic resonance image may have the effect of being the most useful to train the subject or restructure the neurons of the subject to get over the fact that the limb has been removed and also may reduce the amount of pain that the subject experiences.

In another embodiment the magnetic resonance imaging system comprises a head coil configured for acquiring the k-space data of the brain of the subject. In this embodiment the head coil restricts motion or immobilizes the subject's head during the acquisition of the k-space data. This is typical for a head coil. This has the advantage that it may greatly simplify the virtual reality system. For example, the virtual reality system in this case need only present a separate image to each eye of the subject. Because the subject is unable to move his or her head it is not needed to model the change in the images due to the subject moving the head in different directions. Conventional and well-known systems used for providing a projection or image to the subject in a magnetic resonance imaging system may therefore be used. This may include having a separate magnetic resonance image compatible display for each eye or for using a light guide or projection system to provide each eye with an image. There are well developed techniques for bringing an image into the bore of the magnetic resonance imaging for a subject.

In another embodiment execution of the machine-executable instructions further causes the computational system to render the at least one virtual reality motion sequence of the missing limb to the subject using the virtual reality system. In this embodiment, after the at least one virtual reality system has been constructed it is actually presented to the subject using the virtual reality system. This has the effect that it may stimulate the phantom limb functional region of the subject's brain. This may have the effect of reducing any pain experienced by the subject from the loss of the limb.

In another embodiment the medical system further comprises a sensory stimulation system configured to provide sensory stimulation to the complimentary limb. This for example may provide a variety of tactile sensations such as pressure, prickling, tickling, temperature or wetting the surface of the complimentary limb. Execution of the machine-executable instructions further causes the computational system to control the sensory stimulation system to provide sensory stimulation to the complimentary limb during the rendering of the at least a portion of the at least one virtual reality motion sequence of the missing limb. In this embodiment the sensory stimulation is provided to the complimentary limb, however, this is done when the subject sees the missing limb moving in the virtual reality system. Although the sensory stimulation is provided to the complimentary limb, the subject's brain may associate this sensory stimulation with the missing limb and this may also help to reduce any pain experienced by the subject.

In another embodiment execution of the machine-executable instructions further causes the computational system to acquire control k-space data descriptive of the phantom limb functional region by controlling the magnetic resonance imaging system with the pulse sequence commands during rendering of the at least one virtual reality motion sequence of the missing limb. Execution of the machine-executable instructions further causes the computational system to reconstruct a control functional magnetic resonance image from the control k-space data. Execution of the machine-executable instructions further causes the computational system to repeat the machine-executable instructions at timing intervals greater than 2 weeks to obtain the control functional magnetic resonance image as a function of time to form a control functional magnetic resonance image sequence. This embodiment may be beneficial because it may provide for a means of noting the effectiveness of presenting the virtual reality motion sequences to the subject in a measurable fashion. This may for example be useful in determining when to modify the at least one virtual reality motion sequence.

During the acquisition of the control k-space data there may be additional magnetic resonance images acquired; such as, for example, a magnetic resonance image used to measure proton density or other magnetic resonance image which shows the detailed structure of the subject's brain. This may enable location of the phantom limb functional region when there is a time interval between acquisitions. There is however a multitude of different variations on how this could be performed. The skilled person is aware of when such anatomical or scouting images should be performed.

In another embodiment the memory further contains an artificial intelligence module configured to output a progress score in response to receiving the control functional magnetic resonance image sequence as input. The progress score is descriptive of a decrease in neural activity in the phantom limb phantom limb functional region. Execution of the machine-executable instructions further causes the computational system to receive the progress score in response to inputting the control functional magnetic resonance image sequence into the artificial intelligence module. This embodiment may be beneficial because the artificial intelligence module may be used for assessing the effectiveness of presenting the at least one virtual reality motion sequence to the subject.

The artificial intelligence module could for example be a convolutional neural network designed for image classification with its output layer trained to assign the progress score instead of the image classification. For example, the VGG family of neural networks such as VGG-11, VGG-13, or VGG-16 would be suitable. Other suitable types of image recognition networks would be the ResNet-50) neural network. For example, instead of providing specific image classifications the outputs could be trained to output the progress score in binary. Another possibility would be to assign one classification and modify the output layer such that it outputs a continuous value. This continuous value could then also be interpreted as a progress score. There are a variety of ways to configure this in a functional way. For training data various case studies where the control functional magnetic resonance images are collected, a human operator could assign the progress score using a manual assessment in the change of neural activity in the phantom limb functional region. It could for example again be performed by comparing it to a baseline measurement and then assigning it a numerical score.

In another embodiment the medical system further comprises a subject feedback system configured for providing subject feedback data. Execution of the machine-executable instructions further causes the computational system to acquire the subject feedback data using the subject feedback system during acquisition of the phantom k-space data. The numerical score of the repetition-specific movement pattern for the current repetition is modified using the subject feedback data. The subject feedback data could take different forms in different examples. In some examples the subject feedback data is subject sensor data. This may include measurements such as a squeeze ball squeezed by the subject where the subject is able to provide the subject feedback data by squeezing the ball, it may also include sensor measurements of various anatomical functions of the subject such as the heart rate, the breathing rate and/or the skin connectivity. The subject feedback data could in other examples be a quantification or numerical value provided by the subject related to the amount of pain subjectively experienced. For example, the subject feedback data may be quantified using a questionnaire and the data may then be entered later or during the same time and incorporated into the numerical score. This could also be accomplished by for example using verbal input or speech recognition from the subject. For example, the subject could, when he or she experiences a change in the pain level, say a number which indicates the pain level. As this changes then the system can automatically track this and provide the subject feedback data indicating the subject's verbal cues. This embodiment may have the benefit that not only the brain activity measurements are used to choose movement parameters for the missing limb, but also other activity or perception of the subject.

In another embodiment the varied movement parameters comprise any one of the following: a type of motion, a type of exercise, a movement speed, a simulated movement frequency or repetition rate, a speed of motion presentation, and a combination of motions. The type of motion may indicate the type of joint movements of the missing limb that are presented. The type of exercise may for example indicate the type of repetitious movements that the rendering of the missing limb is depicted to move. The movement speed may be how fast or rapid these movements are performed. The simulated movement frequency or repetition rate may indicate how quickly or how often particular movements are repeated. The speed of motion presentation is similar to the movement speed. The combination of motions is preferably from a library of gestures and/or motions. For example, during each of the repetitions one or several entries from this library of gestures could be chosen and presented. By using different combinations of the motions in the library of gestures which are the most effective could be selected and/or ranked. This embodiment is beneficial because it may provide for an effective means of determining the motions of the missing limb which greatly stimulate the phantom limb functional region.

In another embodiment execution of the machine-executable instructions further cause the computational system to transmit at least one virtual reality motion sequence to an external virtual reality system. The external virtual reality system as used herein encompasses a virtual reality system that is not part of the medical system. For example, the machine-executable instructions may cause the computational system to transfer the at least one virtual reality motion sequence to the external virtual reality system via a network connection. This may be beneficial because the subject may then use the at least one virtual reality motion sequence without having to use the virtual reality system of the medical system. The external virtual reality system may in some instances also be more sophisticated than the one used for the medical system. In the medical system there may be a head coil which immobilizes the head. Whereas an external virtual reality system may for example be a commercial virtual reality system such as used with a computer or console game system that is able to determine and track the location of the person's head within a virtual reality world or depiction. The use of the external virtual reality system may enable the subject to use the at least one virtual reality motion sequence in a variety of different situations and settings using the virtual reality system that they already own.

In another embodiment the medical system further comprises a motion tracking system configured for generating tracking data descriptive of motion of the complimentary limb. Execution of the machine-executable instructions further causes the computational system to acquire the tracking data during acquisition of the reference k-space data. The tracking data is used to control the virtual reality system to generate images of the complimentary limb moving during acquisition of the reference k-space data. This embodiment may be beneficial because having the virtual reality image match the actual motion of the complimentary limb may result in better stimulation of the complementary limb functional region in the brain. The motion tracking system may take different forms in different examples. For example, there may be an optical system which is used to track the location of the complimentary limb, for example, a 3D camera or a combination of several cameras. There are a variety of commercial systems available which may do this without modification such as the well-known Xbox Kinect system.

In another embodiment the pulse sequence commands are according to a bold magnetic resonance imaging protocol.

In another embodiment the pulse sequence commands are according to a T2-star weighted gradient echo EPI magnetic resonance imaging protocol.

In another aspect the invention provides for a method of using a magnetic resonance imaging system configured for acquiring k-space data of a brain of a subject with a missing limb and a complimentary limb and comprises a virtual reality system configured for presenting a virtual reality image to the subject during acquisition of the k-space data. The method comprises acquiring baseline k-space data by controlling the magnetic resonance imaging system with the pulse sequence commands. The pulse sequence commands are configured to control the k-space data according to a functional magnetic resonance imaging protocol for measuring brain activity. The method further comprises reconstructing a baseline functional magnetic resonance image from the baseline k-space data. The method further comprises acquiring reference k-space data by controlling the magnetic resonance imaging system with the pulse sequence commands. The method further comprises controlling the virtual reality system to generate images of the complimentary limb moving during acquisition of the reference k-space data.

The method further comprises reconstructing a reference functional magnetic resonance image from the reference k-space data. The method further comprises identifying a complementary limb functional region in the brain by comparing the baseline functional magnetic resonance image and the reference functional magnetic resonance image. The method further comprises determining a phantom limb functional region in the brain by playing brain symmetry to the complementary limb functional region. The method further comprises repetitions of acquiring phantom limb k-space data descriptive of the phantom limb functional region by controlling the magnetic resonance imaging system with the pulse sequence commands. As part of these repetitions the method further comprises controlling the virtual reality system to generate images of the missing limb moving during acquisition of the phantom limb k-space data using repetition-specific movement patterns of the missing limb with varied movement parameters for each repetition. As part of these repetitions the method further comprises reconstructing a phantom limb functional magnetic resonance image from the phantom limb k-space data. There is a phantom limb functional magnetic resonance image for each of these repetitions. As part of these repetitions the method further comprises assigning a numerical score to the repetition-specific movement pattern for the current repetition by detecting neural activity in the phantom limb functional region of the phantom limb functional magnetic resonance image. The score is representative of neural activity in the phantom limb functional image region.

The method further comprises constructing at least one virtual reality motion sequence of the missing limb by selecting the varied movement parameters that maximize neural activity in the phantom limb functional region using the numerical score for each repetition of the specific movement patterns. The advantages of this have been previously discussed. The method further comprises rendering the motion sequence of the missing limb for the subject by an external virtual reality system. For example, the computational system could transfer the motion sequence for the missing limb for the subject to an external virtual reality system. This might be a virtual reality system available at a therapist, it might be a virtual reality system that the subject has access to with a computer, it could also be an external virtual reality system which is part of a console gaming system. The advantages of rendering the motion sequence using the external virtual reality system are that the other components of the medical instrument, such as the magnetic resonance imaging system and a virtual reality system which is compatible with the magnetic resonance image are not needed.

In another embodiment the external virtual reality system is configured to render the motion sequence of the missing limb for the subject during a video game. One factor which may increase success is if the subject is motivated to use the extended virtual reality system to render the motion sequence of the missing limb. By incorporating this into a video game the subject may find this more interesting and spend more time doing this. It may therefore have the effect of increasing its effectiveness.

In another aspect the invention provides for a computer program product that comprises machine-executable instructions for performing an embodiment of the invention.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a computational system of a general-purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A "user interface' may also be referred to as a 'human interface' device." A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data, Examples of a display include, but are not limited to: a computer monitor, a television screen, a touch screen, tactile electronic display, Braille screen.

Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan. Magnetic resonance data is an example of tomographic medical image data.

A Magnetic Resonance image (MRI) or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF EMBODIMENTS

Like numbered elements in these figures are either equivalent elements or perform the same function. Elements which have been discussed previously will not necessarily be discussed in later figures if the function is equivalent.

Figure 1:
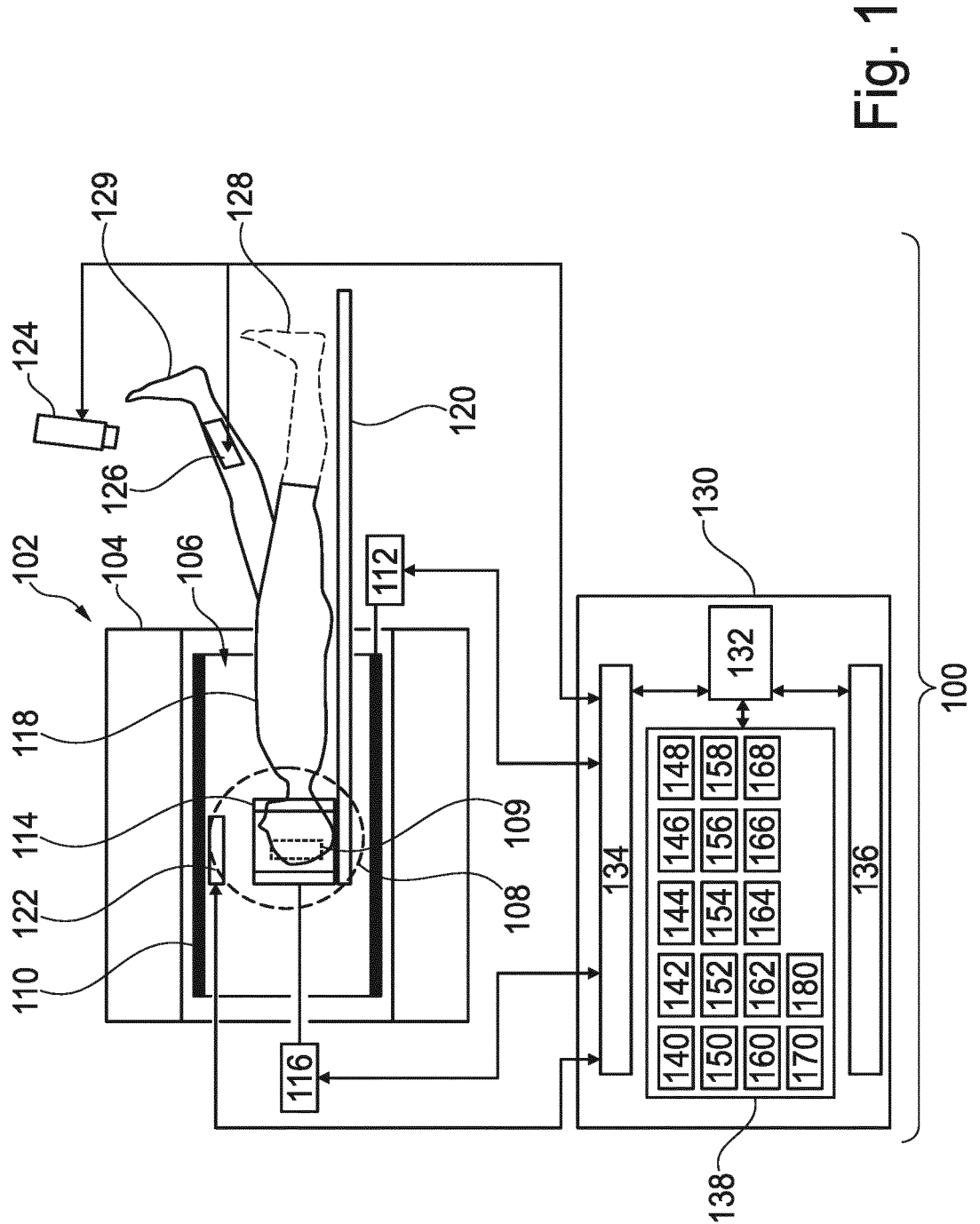
FIG. 1 illustrates an example of a medical instrument.

FIG. 1 illustrates an example of a medical instrument 100. The medical instrument 100 is shown as comprising a magnetic resonance imaging system 102 as well as a computer 130.

The magnetic resonance imaging system 102 comprises a magnet 104. The magnet 104 is a superconducting cylindrical type magnet with a bore 106 through it. The use of different types of magnets is also possible: for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used to provide for freer motion of a subject such as when moving the complementary limb 129. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 106 of the cylindrical magnet 104 there is an imaging zone 108 where the magnetic field is strong and uniform enough to perform magnetic resonance imaging. A field of view 109 is shown within the imaging zone 108. The magnetic resonance data that is acquired typically acquired for the field of view 109. The field of view 109 is shown as imaging a brain volume of a subject 118 which is shown as being supported by a subject support 120.

Within the imaging zone 108 the head of the subject 118 is within a head coil 114. This enables the imaging of a field of view 109.

Above the head of the subject 118 is a virtual reality system 122 which in this example arc separate displays for each eye of the subject. Various types of displays could be used such as mirrors which reflect a view of a projection outside of the bore 106 of the magnet 104 as well as also providing for a magnetic resonance compatible display directly above the eyes of the subject 118. Other types of stimuli such as sound or also tactile stimulation may also be provided.

Within the bore 106 of the magnet there is also a set of magnetic field gradient coils 110 which is used for acquisition of preliminary magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. In this case the radio-frequency coil 114 is a head coil. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels.

In the case when a head coil 114 is being used, this may simplify the construction of a virtual reality system greatly. To perform functional magnetic resonance imaging the head of the subject 118 may be immobilized or the subject 118 decides or is encouraged to remain as motionless as possible. The head coil 114 may comfortably restrain the head of the subject 118. This means that the virtual reality system 122 does not need to account for motions of the subject's head, it merely present different images to each eye of the subject 118. This could for example be done by having two magnetic resonance imaging compatible screens, one of which is visible to each eye; a projection system can also be used to locate the virtual reality system outside of the bore 106 of the magnet 104. In this case mirrors or light pipes could be used to provide the image to the eyes of the subject 118.

As was mentioned previously, the magnetic resonance imaging system 102 may be restrictive and it may not always be possible for the subject 118 to move the complimentary limb 129. In this example the feet of the subject 118 extend outside of the bore 106 and the subject is able to move his legs 128, 129. In this example the leg labeled 128 is the missing limb and the complimentary limb is limb 129. The subject in this case is able to move the complimentary limb 129. There is an optional motion tracking system 124 optionally able to acquire motion data 124. This could be used to render an image of the complimentary limb 129 during the phase of calibrating the system. The magnetic resonance imaging system 102 is also shown as optionally comprising a sensory stimulation system 126. This provides, for example, a tactile stimulation to the complimentary limb 129. This may be used for example when performing a simulation of the missing limb 128 moving. Although the sensory stimulation is on the opposite leg, this may still assist the brain in believing the sensation that the missing limb 128 is there.

In alterative examples, element 126 may represent a sensor system for making a measurement descriptive of a physiological property or value of the subject. For example, the heart rate, breathing rate, or skin conductivity could also be used to evaluate the subject's response to a particular motion pattern of the missing limb. Such data could be used to modify the value of the numerical score. Linguistic feedback such as a verbal description of phantom limb pain experienced or tactile feedback as provided by a squeeze ball could also be incorporated into the numerical score.

The computer 130 could, for example, be a distributed computing system as well as a computer located remotely or via a cloud web service. The computer 130 could also be a workstation or computer used by a radiologist or other medical professional. The computer 130 could also be a control system for a magnetic resonance imaging system. The computer 130 is shown as comprising a computational system 132 that is intended to represent one or more computational systems that may be located in one or more locations. The computational system 132 is connected to a hardware interface 134 and an optional user interface 136. The hardware interface 134 enables the computational system 132 to control other components of the medical instrument 100 such as the magnetic resonance imaging system 102. The user interface 108 may enable an operator to control and operate and interact with the medical instrument 100.

The computational system 132 is further shown as being in communication with a memory 138. The memory 138 is intended to represent various types of memory which may be able to communicate with the computational system 132. The memory 138 is shown as containing machine-executable instructions 140. The machine-executable instructions 130 enable the computational system 132 to perform various tasks such as controlling other components of the medical instrument 100 as well as performing numerical and image processing tasks.

The memory 138 is shown as containing optional scout scan pulse sequence commands 142. This could be used to acquire scout scan k-space data, which is then reconstructed into a scout image 144. The scout image 144 may not necessarily necessary in all examples. However, the scout image 144 could be used for correctly identifying the location of the brain and could also be used during the portions of when the various functional regions of the brain are determined. For example, it may provide a proton density image which provides a very good structural image of how the brain is structured, which may be useful in using the mirror imaging technique to transfer one functional region from one hemisphere of the brain to the other.

The memory 138 is further shown as containing pulse sequence commands 146 that are according to a functional magnetic resonance imaging protocol that is used for measuring the brain activity of the subject 118. The pulse sequence commands 146 are used throughout and it is understood that the various minor parameters, such as adjustments of the field of view 109 and other properties, can take place. The memory 138 is further shown as containing baseline k-space data 148 that is acquired from the subject 118. This is for example acquired when the subject is instructed to remain still so that a 20) baseline measurement of brain activity can be measured or determined. The baseline k-space data 148 is then used to reconstruct a baseline functional magnetic resonance image 150. The memory 138 is then shown as containing reference k-space data 152 which was acquired when the subject 118 was shown images of the complimentary limb moving with the virtual reality system 122.

The memory 138 is shown as further containing a reference functional magnetic resonance image 154 constructed from the reference k-space data 152. The memory 138 is then further shown as containing a location of the complementary limb functional region 156 within the subject's 118 brain. This location is identified in the reference functional magnetic resonance image 154 and indicates the region of the brain of the subject that is active when the complimentary limb 129 moves, as is depicted in FIG. 1, or is depicted as moving by the virtual reality system 122. The memory 138 is further shown as containing a location of a phantom limb functional region 158. This was obtained by using brain symmetry to transfer the location of the complementary limb functional region 156 from one hemisphere to the other hemisphere of the subject's brain. A previous image such as the scout image 144 could be used to identify the structure of the subject's brain and create a mapping between the two. After the identification of the phantom limb functional region 158 a variety of experiments are performed to see which movements of the missing limb 128 in virtual reality most stimulate the brain of the subject 118.

The memory 138 is shown as containing an optional database or dictionary of limb motions 160. These may be used to construct a repetition-specific movement pattern 162 for the missing limb 128 that is rendered with the virtual reality system 122. The memory 138 is containing a rendering of the repetition-specific movement patterns 164 that is then rendered on the virtual reality system 122. During each repetition phantom limb k-space data 166 is acquired as the repetition-specific movement pattern is rendered. The phantom limb k-space data 166 is then reconstructed into a phantom limb functional magnetic resonance image 168. The location of the phantom limb functional region 158 is known and this is used to examine this specific region in the phantom limb functional magnetic resonance image 168 and for example a numerical score 170 is assigned to each particular phantom limb functional magnetic resonance image 168 based on how much neural activity is in the phantom limb functional region 158.

This for example could be done by taking the intensity in each voxel in the phantom limb functional region 158 and summing these to acquire an aggregate score. There are also a variety of different techniques that could be used to assign a numerical score based on the voxels within the phantom limb functional region 158. Once the iterations are complete then there is then a collection of phantom limb functional magnetic resonance images 168 with numerical scores attached to them 170. Using this information, a virtual reality motion sequence 180 is constructed. The virtual reality motion sequence 180 has the motions selected such that the activity within the phantom limb functional region 158 is maximized or increased. This results in a virtual reality motion sequence 180 which is specific to the subject 118 and which does a particularly good job of stimulating the portion of the brain responsible for the missing limb 128.

Figure 2:
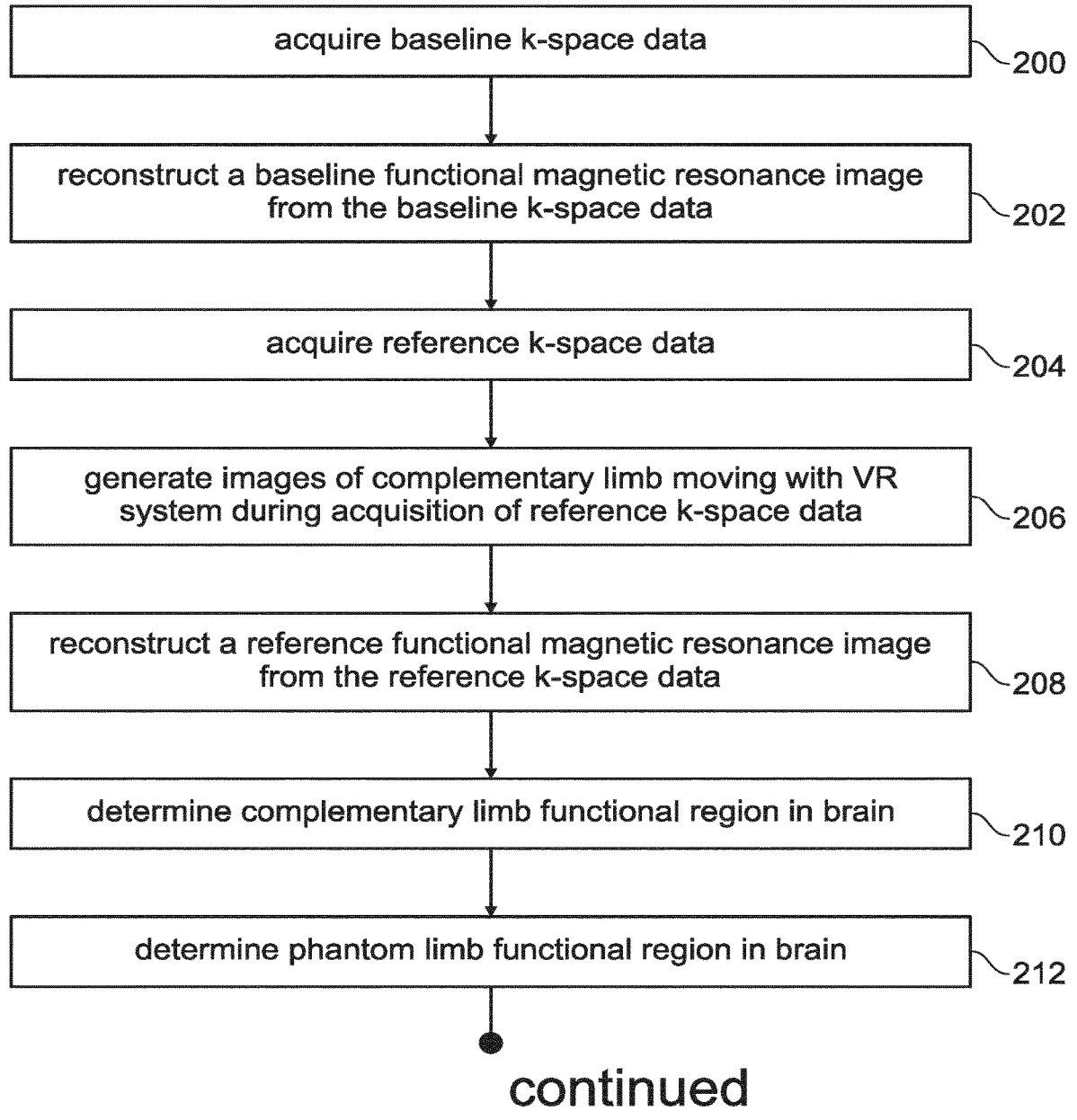
FIG. 2 shows a flow chart which illustrates a method of using the medical instrument of FIG. 1.
Figure 2:
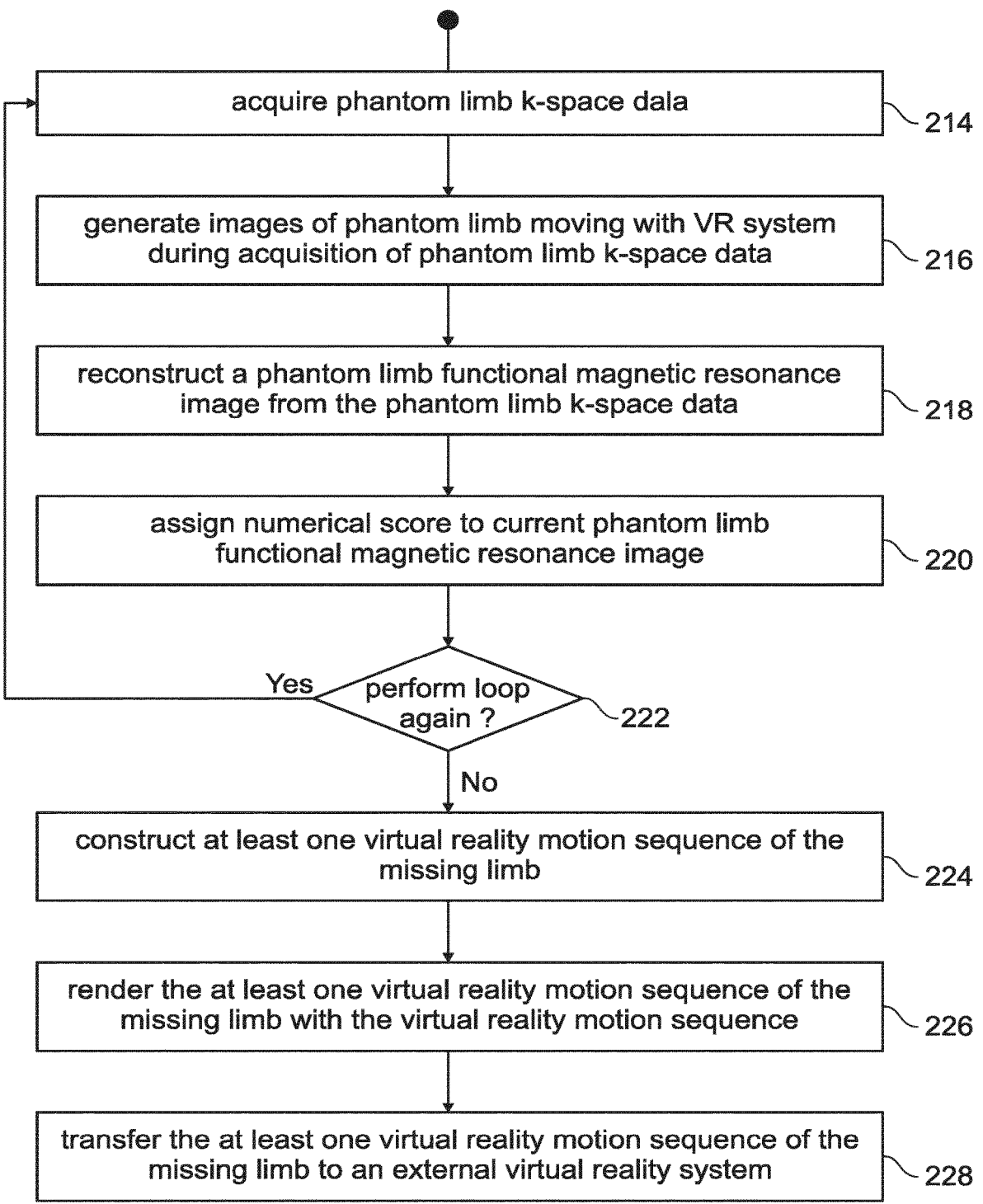

FIG. 2 shows a flowchart which illustrates a method of operating the medical instrument of FIG. 1. First, in step 200, the magnetic resonance imaging system 102 is controlled with the pulse sequence commands 146 to acquire the baseline k-space data 148. Next, in step 202, the baseline functional magnetic resonance image 150 is reconstructed from the baseline k-space data 148. Then, in step 204, reference k-space data 152 is acquired by controlling the magnetic resonance imaging system 102 with the pulse sequence commands 146. Next, in step 206, the virtual reality system 122 is controlled to generate images of the complimentary limb 129 moving during acquisition of the reference k-space data 152.

In step 208, the reference functional magnetic resonance image 154 is reconstructed from the reference k-space data 152. In step 210, the location of the complementary limb functional region 156 is identified in the brain by comparing the baseline functional magnetic resonance image 150 and the reference functional magnetic resonance image 154. In step 212 the location of the phantom limb functional region 158 is determined by applying brain symmetry to the complementary limb functional region 156. In steps 214, 216, 218, 220, 222 a number of iterations are performed. Starting this iteration in step 214 phantom limb k-space data 166 is acquired by controlling the magnetic resonance imaging system 102 with the pulse sequence commands. Next, in step 216, the virtual reality system 122 is controlled to generate images of the missing limb 128 moving during acquisition of the phantom limb k-space data 166 using a repetition-specific movement pattern of the missing limb with varied movement parameters for each repetition. Next, in step 218, the phantom limb functional magnetic resonance image 168 is reconstructed from the phantom limb k-space data 166. Then, in step 220, a numerical score is assigned to the repetition-specific movement pattern for the current repetition by detecting neural activity in the phantom limb functional region of the phantom limb functional magnetic resonance image 168.

Step 222 is a decision box and the decision is should the loop be performed again, if the answer is yes then the method proceeds to step 214 and this process is repeated. If the answer is no, the method proceeds then to step 224. In step 224 at least one virtual reality motion sequence of the missing limb is constructed by selecting the varied movement patterns that maximize neural activity in the phantom limb functional region using the numerical score for each repetition-specific movement pattern. In other words, a virtual reality motion sequence is customized or constructed for the subject 118 by choosing those movements which were tried previously and elicited the largest neural response in the phantom limb functional region.

Once the at least one virtual reality motion sequence 180 has been reconstructed there are a number of possibilities. In optional step 226 the machine-executable instructions further cause the computational system to render the at least one virtual reality motion sequence 180 to the subject using the virtual reality system 122. In this optional step, after the optimal or improved motion sequence has been constructed, it is then presented to the subject 118 to help the subject 118 overcome any phantom limb pain. Another option is presented in optional step 228. In optional step 228 the at least one virtual reality motion sequence 180 is transferred to an external virtual reality system. This optional step may also be beneficial because once the optimal or the virtual reality motion sequence 180 has been determined it does not need to be done or performed using the same virtual reality system 122 here. For example, magnetic resonance imaging systems are very expensive, and it is not necessary to take time from the magnetic resonance imaging system 102 for any stimulation or training for the subject 118. The external virtual reality system could for example be a virtual reality system that the subject 118 has at home for a computer or even a console gaming system.

Figure 3:
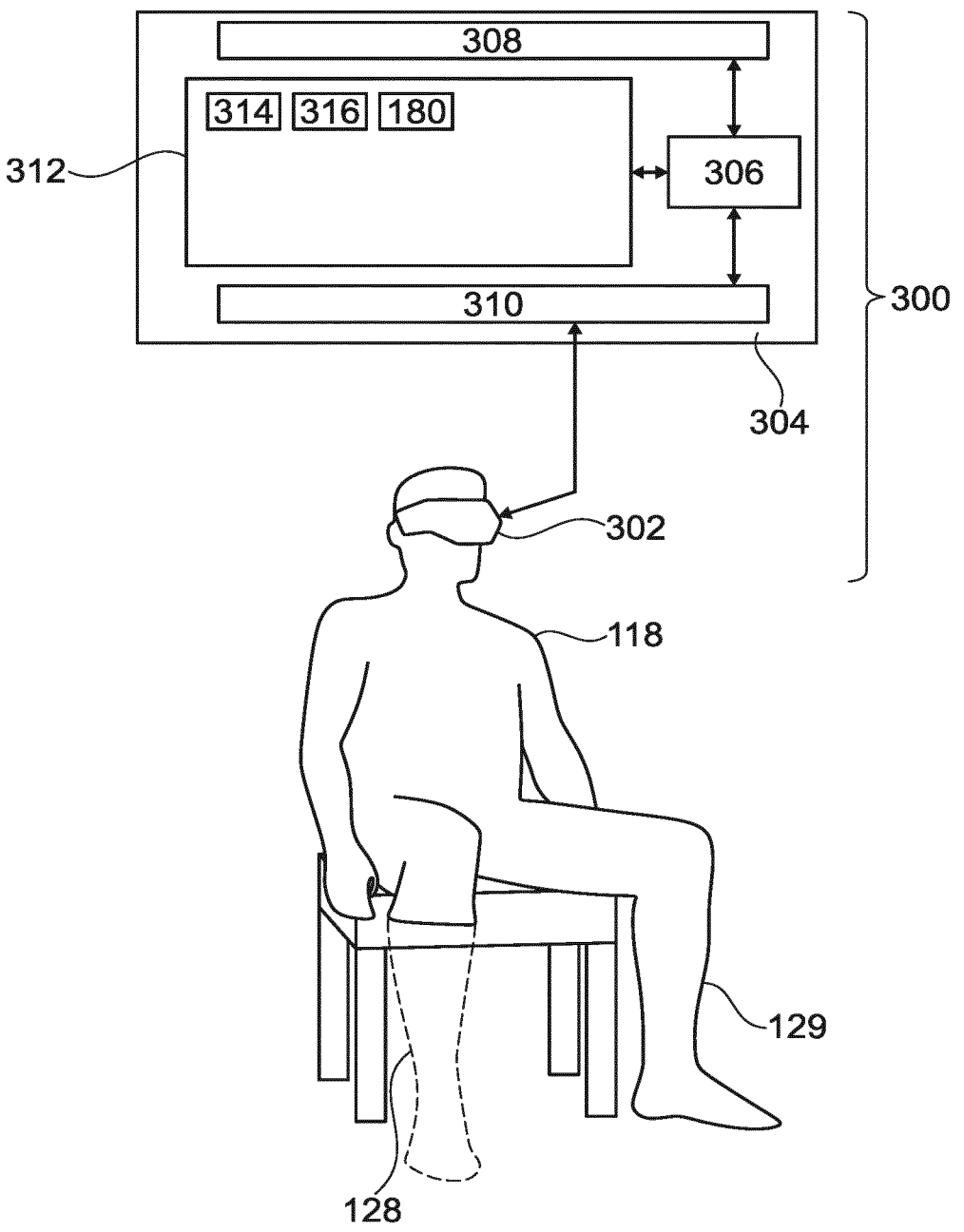
FIG. 3 illustrates an example of an external virtual reality system being used by a subject.

FIG. 3 illustrates an example of an external virtual reality system 300. It comprises a headset 302 worn by the subject 118 and an external computer system 304. The external computer system 304, which could for example be a home personal computer or a video game system, or a console game system, is shown as comprising a computational device 306 in communication with a network interface 308, a user interface 310 and a memory 312. The network interface 308 could for example be used to receive the virtual reality motion sequence 180 and place it in the memory 312. The memory 312 is shown as containing additional machine-executable instructions 314 which enable the computational device 306 to use the interface 310 to render images using the headset 302. This provides the virtual reality experience to the subject 118.

The additional machine-executable instructions 314 could for example be used to render the virtual reality motion sequence 180 using the headset 302. Another possibility is that the memory 312 may contain a video game 316. The machine-executable instructions 314 are then able to integrate the virtual reality motion sequence 180 into an execution or plane of the video game 316. This may for example make it more enjoyable for the subject 118 to play the virtual reality motion sequence 180.

Phantom limb pain (PLP) is a frequent painful sensation perceived within the absent part of the amputated extremity. PLP can be as stressing phenomenon that becomes chronic and affects the patient's quality of life. The etiology of PLP is multifactorial its mechanism also includes cortical reorganization, peripheral-nerve hyperexcitability (PNH), central sensitization, and visual-proprioceptive dissociation. Mirror therapy (MT) is currently the most used treatment for PLP. Some of the shortcomings of the MT can be overcoming by virtual reality applications (VR). In the current VR stimulation detection of the movements of the intact lower limb is done and displayed as movements of the phantom limb. Disadvantages of current VR stimulation are: lack of the use of individual patient characteristics, the information of the effect of the stimulation is based on subjective judgment. Another disadvantage is that currently brain activity of the area representing the amputated limb, as well as the neuronal area representing the displayed limb are not being used in the stimulation as input to verify the effect and accuracy of the intervention. Examples may provide for a more accurate management of PLP by using a personalized VR simulation stimulation program and functional real time MR brain imaging. Additionally, subjective patient input may be used. The VR stimulation may be tuned to the personal needs of the patient and individual response (real time neural activity of the patient) to the VR program as obtained by functional neuroimaging data Personalization and optimization of the VR stimulation helps to increase compliance of the stimulation and consequently its effectiveness. Additional examples that describe additional features are also added.

Phantom limb pain (PLP) is often defined as "pain that is localized in the region of the removed body part". The onset of this pain most often occurs soon after surgery. It can feel like burning, twisting, itching or pressure. Phantom limb pain (PLP) occurs in 50%-80% of limb amputees and is known to be highly fluctuant. It is estimated that, by 2050, there will be 3.6 million amputees in the U.S. Therefore, it has become increasingly important to understand and properly manage PLP.

The large variation in symptomatology suggests a multifactorial origin of phantom phenomena. Central alterations are of special importance for its presence, with the primary somatosensory cortex playing a key role in the perceived intensity of PLP. It has been reported that dysfunctional plastic changes after amputation might prevent or reduce PLP.

Regular pain treatment is seldom effective for PLP. Pharmacologic interventions are not entirely effective and may have adverse and side effects. Alternatively, nonpharmacologic treatments are currently used to treat PLP, such as acupuncture, transcutaneous electrical nerve stimulation, deep brain stimulation, electroconvulsive therapy, and transcranial magnetic stimulation.

Since PLP's mechanism includes cortical reorganization, peripheral-nerve hyperexcitability (PNH), central sensitization, and visual-proprioceptive dissociation, mirror therapy (MT) has become a popular treatment more than two decades ago.

During MT, the patient is asked to place the amputated limb (missing limb 128) behind a mirror. The patient then moves and watches the reflection of the intact limb in the mirror. It creates a visual illusion of the movement of the amputated side. In terms of the mechanisms observing mirror movements have been shown to activate brain's motor network. Mirror therapy might eliminate the mismatch between motor signals and inappropriate visual feedback from the missing limb 128 in amputees suffering from PLP. The visual illusion generates positive feedback to the motor cortex, helping to block the pain cycle.

However, traditional mirror therapy treatment has limitations in meeting this objective, since the intervention relies on the physical and functional features of an intact limb (complementary limb 129), which do not necessarily match the perceived characteristics of the phantom limb. MT may use filming with a camera of an intact limb for movement representation on a monitor. First this is restricting the treatment to unilateral amputees. The current MT treatments includes physical interventions which in some cases results in an adverse situation such as pain increase or nausca.

In recent years, associated techniques such as imagery virtual reality (VR) and immersive therapies have shown to offer a potential alternative to traditional MT. Virtual Reality has the potential of creating a more 'sophisticated' immersive form of MT.

In the VR stimulation, the mirror image is replaced by a computer graphical representation of the lost limb. Detection of the movements of the intact limb is done and represented as movements of the phantom limb. Another advantage is that VR may also incorporate gaming elements into PLP treatment to theoretically increase participants' enjoyment of the experience, that can help to potentially improve adherence, and can be configured to multiple kinds of amputations (e.g., upper body, lower body, bilateral amputee populations).

The literature shows that there is a clear relationship between subjective pain rating and above-mentioned VR stimulation results as well as between activity in cortical (remapped) brain areas and pain ratings.

Mirror therapy in which patient observe and engage in the intact limb mirrored movements is currently the most used treatment for PLP. However, traditional MT treatment has limitations in meeting this objective.

Some of the shortcomings of the MT can be overcome by virtual reality applications (VR). In the current VR stimulation detection of the movements of the intact lower limb is done and displayed as movements of the phantom limb.

Still, the current VR approach is limited by the lack of the use of individual patient characteristics Another disadvantage is that current VR stimulation is that the information of the effect of the stimulation is based on patient's perception related to the phantom limb and on subjective judgment.

Another problem is given the technical potential, that currently brain activity of the area representing the amputated limb, as well as the neuronal area representing the displayed (symmetric still-present) limb on the lateral side of the body, are not being used in the stimulation as input to verify the effect and accuracy of the intervention.

Some examples may provide accurate management of PLP. Concretely, some examples provide a reinforcement procedure that may be useful for treatment of PLP using MR brain imaging together with a personalized VR simulation program stimulation.

This approach may benefit from the use of functional MR neuroimaging for fine tuning the VR simulation program to the personal activated brain areas, and individual response to the VR stimulation. Additionally, subjective patient input is used. Personalization and optimization of the VR stimulation helps to increase compliance of the stimulation and consequently its effectiveness.

The method and system of examples may comprise one or more of the following elements:

A-Software/computer (130)) unit:
- To generate a virtual image of the patient's own body, including missing limb.
- To generate visual simulation: Creation of simulation program of exercises and movements of movements of both intact and missing limbs. Creation of simulation of all-body action B-Virtual Reality unit (122):
- To provide a virtual reality immersive simulation-program (obtained from software unit). Immersive VR technology that simulates patient's limb motions and show him or her a pair of intact limbs moving at the same time. VR allows the reproduction of the situation and context in a life-like settings.
- VR unit is used within the MRI environment: evaluation and tuning/tailoring of VR stimulation
- VR unit is also used outside MRI scan: reinforcement of stimulation (delivered VR stimulation on regular basis)

C-MRI scan unit (MRI system 102): Monitoring unit/screening unit:
- MRI scan: functional real-time MRI brain scan monitoring the effect of VR stimulation (immediately in real-time) on the neural areas associated with pain and perception of phantom limb (individualized for the patient), such as the somatosensory cortex or parts of it.
- Simulation images are viewed by the patient through the VR unit while being in the scanner.
- Communication system to receive the input/images from the fMRI:
- Software for analysis of fMRI images D-Processing unit (computer 130):
- To determine and evaluate the response of the patient to the VR stimulation (MRI environment).

- To create a rating scale of the effect of the VR: assessment of the effect and the effectiveness of VR stimulation-program.
- To tailor the VR stimulation (simulation) to the patient's response: optimization and personalized the VR stimulation to the patient's needs E-Controller Unit (computer 130):
- A controller in communication with VR unit: adaptation of the VR stimulation program according with the individual assessment (patient's response)

Within examples there may be a procedure that improves and enhances efficacy and effectiveness of VR reality stimulation for PLP. Concretely it may be a method and system for personalization of a Virtual Reality stimulation program (personalized simulations/animations) in combination with real-time fMRI.

A realistic and immersive sensation may be created with virtual reality simulation inside the MRI scanner. The functional MRI provides information of the patient's neural correlates of the phantom limb (missing limb 128): functional changes in cortical areas of interest (e.g. somatosensorimotor cortex) can be characterized in response to the direct application of virtual reality simulation, and also information regarding the perception of the visualization of an intact limb and missing limb as well as virtual movements of both. The stimulation-program is based on the real-time neural activity of the patient to the VR stimulation, in other words, the simulation-program is personalized based on the real-time neural activity of the patient to the VR simulation, i.e. a specific simulation movement or exercise may help to reduce the perception of pain, tailor the VR stimulation to individual neuronal responses, helps to increase its potential.

In one example, motion-related brain areas in the left and right cortices are measured and assessed first for their symmetry and second, in case of asymmetry, which motor-related brain activation is still present in cortex of the affected side (corresponding to phantom limb) of the brain.

The subject may be asked to actively think about making movements of the phantom limb while the subject is in the MR scanner. If such imagery does successfully entail neural activation (as picked up by the scanner) within the affected cortex, then use this activity to enhance or decrease it through neuro-feedback. Using neurofeedback there is a reward for brain activity in the region of interest that engage the pain-related phantom-limb neurons.

In a further example, after this has been done for thousands of subjects subtending a normative data table, use average data to advise a radiologist on brain areas may still be present.

In a further example, it is determined from measured brain activity on either side in the motor cortices how far a patient is in the process of remapping of the motor cortices. If loss of sensory feedback causes a degradation of sensory-motor representations relevant to the missing limb, interventions that provide feedback relevant to the planned action of the missing limb ought to reduce pain.

In another example presentation of the at least one virtual reality sequence is followed by MR brain scans recorded longitudinally over months of viewing the VR sequence. Every predetermined period of time (i.e. every two months) the patient undergoes the same process/protocol: evaluation of PLP and further tailoring of VR stimulation. Determine through MR scanning the extent or rate of cortical remapping for a particular subject. Use this as a parameter to assess efficacy of viewing the VR sequence longitudinally.

In another example, the personalization and optimization of VR sequences might enhance motivation and compliance to use (performance) VR stimulation outside MRI scan on regular basis, which will result in an increasing of effectiveness. Tailoring (readaptation) of the program may done in an automatic way.

In another example, the objective information provided by the analysis of images of MRI scan, subjective information (patient's experience) may be used. Both objective (patient's neural information) and subjective (patient's perception/feedback) may be used to improve further the effectiveness of the VR stimulation program.

In another example, the method and system (medical instrument 100) include additionally tactile and sensory stimulation: this may be provided during the MRI scan.

In another example, the system (medical instrument 100) may also include additional methodologies for assessment of the effect of VR stimulation: general body reaction or physiological reactions (breathing rate, heart rate) of patient. This includes multimodal assessment (other methodologies and subjective patient's feedback) together with neuroimaging data can be used to provide a more robust evaluation of the effect of the VR simulation program/settings and subsequently to optimize stimulation.

In another example, machine learning or A.I. unit may be used: Information collected for a period of time, could be quantified by means of a pattern index that may be used as indication of the patient's improvement: neurological changes (neurorehabilitation) are compared to initial (reference) state.

In another example, the personalized and optimized VR program is provided outside of the MRI scanner environment. Method and system contain an additional data acquisition unit that collects subjective information/feedback of patient while VR stimulation program is done outside the MRI. This information may be included for further optimization (adjustment) and personalization of the VR stimulation program.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCE SIGNS LIST 100 medical instrument
102 magnetic resonance imaging system
104 magnet
106 bore of magnet
108 imaging zone
109 field of view
110 magnetic field gradient coils
112 magnetic field gradient coil power supply
114 head coil
116 transceiver
118 subject
120 subject support
122 VR system (display)
124 motion tracking system (motion data)
126 sensory stimulation system
128 missing limb
129 complementary limb
130 computer
132 computational system
134 hardware interface
136 user interface
138 memory
140 machine executable instructions
142 scout scan pulse sequence commands
144 scout image
146 pulse sequence commands
148 basline k-space data
150 basline functional magnetic resonance image
152 reference k-space data
154 reference functional magnetic resonance image
156 location of complementary limb functional region
158 location of phantom limb functional region
160 database or dictionary of limb motions
162 repetition specific movement pattern
164 rendering of repetition specific movement pattern
166 phantom limb k-space data
168 phantom limb functional magnetic resonance image
170 numerical score assigned to phantom limb functional magnetic resonance image
180 virtual reality motion sequence
200 acquire baseline k-space data by controlling the magnetic resonance imaging system with the pulse sequence commands
202 reconstruct a baseline functional magnetic resonance image from the baseline k-space data
204 acquire reference k-space data by controlling the magnetic resonance imaging system with the pulse sequence commands
206 control the virtual reality system to generate images of the complementary limb moving during acquisition of the reference k-space data
208 reconstruct a reference functional magnetic resonance image from the reference k-space data
210 identify a complementary limb functional region in the brain by comparing the baseline functional magnetic resonance image and the reference functional magnetic resonance image
212 determine a phantom limb functional region in the brain by applying brain symmetry to the complementary limb functional region
214 acquire phantom limb k-space data descriptive of the phantom limb functional region by controlling the magnetic resonance imaging system with the pulse sequence commands
216 controlling the virtual reality system to generate images of the missing limb moving during acquisition of the phantom limb k-space data using a repetition specific movement pattern of the missing limb with varied movement parameters for each repetition reconstruct a phantom limb functional magnetic resonance image from the phantom limb k-space data

220 assign a numerical score to the repetition specific movement pattern for the current repetition by detecting neural activity in the phantom limb functional region of the phantom limb functional magnetic resonance image

224 construct at least one virtual reality motion sequence of the missing limb by selecting the varied movement parameters that maximize neural activity in the phantom limb functional region using the numerical score for each repetition specific movement pattern

226 render the at least one virtual reality motion sequence of the missing limb to the subject using the virtual reality system

228 transfer the at least one virtual reality motion sequence to an external virtual reality system

300 external virtual reality system

302 headset

304 external computer system

300 computational device

308 network interface

310 user interface

312 memory

314 additional machine executable instructions

316 video game

The invention claimed is:

1. A medical instrument comprising:

a magnetic resonance imaging system configured to acquire k-space data of a brain of a subject with a missing limb and a complementary limb;

a virtual reality system configured to present a virtual reality image to the subject during acquisition of the k-space data;

a memory configured to store machine executable instructions and pulse sequence commands, wherein the pulse sequence commands are configured to control the magnetic resonance imaging system to acquire the k-space data according to a functional magnetic resonance imaging protocol for measuring brain activity;

a computational system configured to control the medical instrument, wherein execution of the machine executable instructions causes the computational system to:

acquire baseline k-space data by controlling the magnetic resonance imaging system with the pulse sequence commands;

reconstruct a baseline functional magnetic resonance image from the baseline k-space data;

acquire reference k-space data by controlling the magnetic resonance imaging system with the pulse sequence commands;

control the virtual reality system to generate images of the complementary limb moving during acquisition of the reference k-space data;

reconstruct a reference functional magnetic resonance image from the reference k-space data;

identify a complementary limb functional region in the brain by comparing the baseline functional magnetic resonance image and the reference functional magnetic resonance image; and determine a phantom limb functional region in the brain by applying brain symmetry to the complementary limb functional region;

wherein execution of the machine executable instructions causes the computational system to perform repetitions of:

acquiring phantom limb k-space data descriptive of the phantom limb functional region by controlling the magnetic resonance imaging system with the pulse sequence commands;

controlling the virtual reality system to generate images of the missing limb moving during acquisition of the phantom limb k-space data using a repetition specific movement pattern of the missing limb with varied movement parameters for each repetition;

reconstructing a phantom limb functional magnetic resonance image from the phantom limb k-space data; and assigning a numerical score to the repetition specific movement pattern for the current repetition by detecting neural activity in the phantom limb functional region of the phantom limb functional magnetic resonance image, the score being representative of neural activity in the phantom limb functional image region;

wherein execution of the machine executable instructions further causes the computational system to construct at least one virtual reality motion sequence of the missing limb by selecting the varied movement parameters that maximize neural activity in the phantom limb functional region using the numerical score for each repetition of the specific movement pattern.

2. The medical system of claim 1, wherein execution of the machine executable instructions further causes the computational system to render the at least one virtual reality motion sequence of the missing limb to the subject using the virtual reality system.

3. The medical system of claim 2, wherein the medical system further comprises a sensory stimulation system configured to provide sensor stimulation to the complementary limb, wherein execution of the machine executable instructions further causes the computational system to control the sensory stimulation system to provide sensory stimulation to the complementary limb during the rendering of a least a portion of the at least one virtual reality motion sequence of the missing limb.

4. The medical system of claim 2, wherein execution of the machine executable instructions further causes the computational system to:

acquire control k-space data descriptive of the phantom limb functional region by controlling the magnetic resonance imaging system with the pulse sequence commands during rendering of the at least one virtual reality motion sequence of the missing limb; and reconstruct a control functional magnetic resonance image from the control k-space data;

repeat the machine executable instructions at time interval greater than two weeks to obtain the control functional magnetic resonance image as a function of time to form a control functional magnetic resonance image sequence.

5. The medical system of claim 4, wherein the memory further contains an artificial intelligence module configured to output a progress score in response to receiving the control functional magnetic resonance image sequence as input, wherein the progress score is descriptive of a decrease in neural activity in the phantom limb functional region, wherein execution of the machine executable instructions further causes the computational system to receive the progress score in response to inputting the control functional magnetic resonance image sequence into the artificial intelligence module.

6. The medical system of claim 1, wherein the medical system further comprises a subject feedback system configured to provide subject feedback data, wherein execution of the machine executable instructions further causes the computational system to acquire the subject feedback data using the subject feedback system during acquisition of the phantom k-space data, and wherein the numerical score of the repetition specific movement pattern for the current repetition is modified using the subject feedback data.

7. The medical system of claim 1, the varied movement parameters comprising at least one of the following: a type of motion, a type of exercise, a movement speed, a simulated movement frequency, or repetition rate.

8. The medical system of claim 1, wherein execution of the machine executable instructions further causes the computational system to transfer the at least one virtual reality motion sequence to an external virtual reality system.

9. The medical system of claim 1, wherein the medical system further comprise a motion tracking system configured to generate tracking data descriptive of motion of the complementary limb, wherein execution of the machine executable instruction further causes the computational system to acquire the tracking data during acquisition of the reference k-space data, and wherein the tracking data is used to control the virtual reality system to generate images of the complementary limb moving during acquisition of the reference k-space data.

10. The medical system of claim 1, wherein the pulse sequence commands are according to a blood oxygen level dependent (BOLD) magnetic resonance imaging protocol or a T2-star weighted gradient echo EPI magnetic resonance imaging protocol.

11. A method of using a magnetic resonance imaging system configured to acquire k-space data of a brain of a subject with a missing limb and a complementary limb and a virtual reality system configured to present a virtual reality image to the subject during acquisition of the k-space data; wherein the method comprises:

acquiring baseline k-space data by controlling the magnetic resonance imaging system with pulse sequence commands, wherein the pulse sequence commands are configured to control the k-space data according to a functional magnetic resonance imaging protocol for measuring brain activity;

reconstructing a baseline functional magnetic resonance image from the baseline k-space data;

acquiring reference k-space data by controlling the magnetic resonance imaging system with the pulse sequence commands;

controlling the virtual reality system to generate images of the complementary limb moving during acquisition of the reference k-space data;

reconstructing a reference functional magnetic resonance image from the reference k-space data;

identifying a complementary limb functional region in the brain by comparing the baseline functional magnetic resonance image and the reference functional magnetic resonance image; and determining a phantom limb functional region in the brain by applying brain symmetry to the complementary limb functional region;

wherein the method further comprises repetitions of:

acquiring phantom limb k-space data descriptive of the phantom limb functional region by controlling the magnetic resonance imaging system with the pulse sequence commands;

controlling the virtual reality system to generate images of the missing limb moving during acquisition of the phantom limb k-space data using a repetition specific movement pattern of the missing limb with varied movement parameters for each repetition;

reconstructing a phantom limb functional magnetic resonance image from the phantom limb k-space data; and assigning a numerical score to the repetition specific movement pattern for the current repetition by detecting neural activity in the phantom limb functional region of the phantom limb functional magnetic resonance image, the score being representative of neural activity in the phantom limb functional image region;

wherein the method further comprises constructing at least one virtual reality motion sequence of the missing limb by selecting the varied movement parameters that maximize neural activity in the phantom limb functional region using the numerical score for each repetition of the specific movement pattern.

12. The method of claim 11, wherein the method further comprises rendering the motion sequence of the missing limb for the subject by an external virtual reality system.

13. The method of claim 12, wherein the external virtual reality system is configured to render the motion sequence of the missing limb for the subject during a video game.

14. A computer program product comprising machine executable instructions stored on a non-transitory computer readable medium, wherein the machine executable instructions are executable by a computational system configured to control a medical instrument, wherein the medical instrument comprises a magnetic resonance imaging system configured to acquire k-space data of a brain of a subject with a missing limb and a complementary limb and a virtual reality system configured to present a virtual reality image to the subject during acquisition of the k-space data, wherein execution of the machine executable instructions causes the computational system to:

acquire baseline k-space data by controlling the magnetic resonance imaging system with pulse sequence commands, wherein the pulse sequence commands are configured to control the k-space data according to a functional magnetic resonance imaging protocol for measuring brain activity;

reconstruct a baseline functional magnetic resonance image from the baseline k-space data;

acquire reference k-space data by controlling the magnetic resonance imaging system with the pulse sequence commands;

control the virtual reality system to generate images of the complementary limb moving during acquisition of the reference k-space data;

reconstruct a reference functional magnetic resonance image from the reference k-space data;

identify a complementary limb functional region in the brain by comparing the baseline functional magnetic resonance image and the reference functional magnetic resonance image; and determine a phantom limb functional region in the brain by applying brain symmetry to the complementary limb functional region;

wherein execution of the machine executable instructions causes the computational system to perform repetitions of:

US 12,569,159 B2

27 acquiring phantom limb k-space data descriptive of the phantom limb functional region by controlling the magnetic resonance imaging system with the pulse sequence commands;

controlling the virtual reality system to generate images of the missing limb moving during acquisition of the phantom limb k-space data using a repetition specific movement pattern of the missing limb with varied movement parameters for each repetition;

reconstructing a phantom limb functional magnetic resonance image from the phantom limb k-space data;

assigning a numerical score to the repetition specific movement pattern for the current repetition by detecting neural activity in the phantom limb functional region of the phantom limb functional magnetic resonance image, the score being representative of neural activity in the phantom limb functional image region;

wherein execution of the machine executable instructions further causes the computational system to construct at least one virtual reality motion sequence of the missing limb by selecting the varied movement parameters that maximize neural activity in the phantom limb functional region using the numerical score for each repetition of the specific movement pattern.

15. The computer program product of claim 14, wherein execution of the machine executable instructions further causes the computational system to render the at least one virtual reality motion sequence of the missing limb to the subject using the virtual reality system.

16. The computer program product of claim 14, wherein execution of the machine executable instructions further causes the computational system to:

acquire control k-space data descriptive of the phantom limb functional region by controlling the magnetic resonance imaging system with the pulse sequence commands during rendering of the at least one virtual reality motion sequence of the missing limb; and reconstruct a control functional magnetic resonance image from the control k-space data;

repeat the machine executable instructions at time interval greater than two weeks to obtain the control functional magnetic resonance image as a function of time to form a control functional magnetic resonance image sequence.

17. The computer program product of claim 16, wherein the machine executable instructions include an artificial intelligence module configured to output a progress score in response to receiving the control functional magnetic resonance image sequence as input, wherein the progress score is descriptive of a decrease in neural activity in the phantom limb functional region, wherein execution of the machine executable instructions further causes the computational system to receive the progress score in response to inputting the control functional magnetic resonance image sequence into the artificial intelligence module.

* * * * *